United States Patent [19]

Landis

[11] Patent Number: 4,664,259
[45] Date of Patent: May 12, 1987

[54] NEEDLE CONTAINER AND METHOD FOR PREVENTING ACCIDENTAL CONTACT WITH A NEEDLE

[76] Inventor: Robert Landis, 331 E. 29th St., Apartment 10G, New York, N.Y. 10016

[21] Appl. No.: 903,861

[22] Filed: Aug. 29, 1986

Related U.S. Application Data

[63] Continuation of Ser. No. 733,478, May 13, 1985, abandoned.

[51] Int. Cl.⁴ .................................................. B65D 83/10
[52] U.S. Cl. ........................................ 206/365; 206/364; 206/571; 206/370; 206/604; 206/605; 604/162; 604/192; 604/263
[58] Field of Search ............... 206/364, 365, 366, 370, 206/380, 571, 601, 604, 605, 459, 438; 604/17, 162, 192, 197, 263

[56] References Cited

U.S. PATENT DOCUMENTS

| | | |
|---|---|---|
| 1,779,451 | 10/1930 | Sponsel .................... 604/197 |
| 2,953,243 | 9/1960 | Roehr . |
| 3,021,942 | 2/1962 | Hamilton . |
| 3,073,307 | 1/1963 | Stevens . |
| 3,074,542 | 1/1963 | Myerson . |
| 3,255,873 | 6/1966 | Speelman ................ 206/366 |
| 3,294,231 | 12/1966 | Vanderbeck . |
| 3,323,523 | 6/1967 | Scislowicz et al. ......... 604/162 |
| 3,329,146 | 7/1967 | Waldman . |
| 3,333,682 | 8/1967 | Burke . |
| 3,367,488 | 2/1968 | Hamilton . |
| 3,485,239 | 12/1969 | Vanderbeck ............... 206/365 |
| 3,610,240 | 10/1971 | Harautuneian ........... 604/162 |
| 3,904,033 | 9/1975 | Haerr .................... 604/162 |
| 3,934,722 | 1/1976 | Goldberg . |
| 3,968,876 | 7/1976 | Brookfield ............... 206/365 |
| 4,113,090 | 9/1978 | Carstens . |
| 4,175,008 | 11/1979 | White .................... 206/459 |
| 4,300,678 | 11/1981 | Gyure et al. ............. 206/364 |
| 4,375,849 | 3/1983 | Hanifl . |
| 4,430,082 | 2/1984 | Schwabacher ............. 604/263 |

*Primary Examiner*—Joseph Man-Fu Moy
*Assistant Examiner*—David T. Fidei
*Attorney, Agent, or Firm*—Morgan & Finnegan

[57] ABSTRACT

A package is described for use with hypodermic needles that assures sterility of the needle prior to use and prevents inadvertent access to the needle after use. In a preferred embodiment a needle housing is hingedly attached to a base so that the housing may be moved from a first position covering the sterile needle to a second position exposing the needle for use to a third position covering the used needle. A hook like protrusion projects from the inside wall of the housing and is biased, in a non-engaging relationship, against the needle prior to use of the needle. When the housing is moved from the second to the third housing position the hook like protrusion engages the needle to prevent movement of the housing and further use of the needle.

27 Claims, 11 Drawing Figures

NEEDLE CONTAINER AND METHOD FOR PREVENTING ACCIDENTAL CONTACT WITH A NEEDLE

This is a continuation of co-pending application Ser. No. 733,478, filed on May 13, 1985, now abandoned.

TECHNICAL FIELD

This invention relates to safe packaging and disposal of needles and, more particularly, to a safety package for preserving sterility of a needle prior to use and for safely disposing of the unsanitary needle after use.

BACKGROUND AND OBJECTS OF THE INVENTION

Use of hypodermic needles presents a clear danger of accidental wounds and infection to all persons exposed to such needles. This danger is particularly acute under prevailing injection conditions where hospital personnel and patients are necessarily exposed to needles. Indeed, under prevailing conditions one or more exposed needles can often be found in the presence of several persons moving about without regard for the potential injury and/or infection that can result from accidental contact with the exposed needle. Thus, it is necessary and desirable to minimize the danger of injury or infection by minimizing the length of time a needle is exposed for use in administering an injection.

PRIOR ART

Several needle packaging structures heretofore provided have concentrated primarily upon preserving needle sterility prior to use and protecting the user during attachment of the sterile needle to a syringe. Examples of such structures are disclosed in:
  (a) U.S. Pat. No. 2,953,243 issued to Roehr for DISPOSABLE NEEDLE ASSEMBLY;
  (b) U.S. Pat. No. 3,074,542 issued to Myerson for PACKAGE FOR HYPODERMIC NEEDLES;
  (c) U.S. Pat. No. 3,294,231 issued to Vanderbeck for DENTAL NEEDLE SHIELD;
  (d) U.S. Pat. No. 3,367,488 issued to Hamilton for HYPODERMIC SYRINGE PACKAGE; and
  (e) U.S. Pat. No. 3,329,146 issued to Waldman for NEEDLE CONTAINER.

Although some of the structures disclosed in these references may also be used for disconnecting a used needle from a syringe for disposal, particularly Roehr 243, Vanderbeck 231 and Waldman 146, none of these structures adequately protects the user's hand during reinsertion of the used needle.

Other attempts to provide protection for a sterile needle prior to use include needle containers which must be at least partially destroyed in order to access the sterile needle. Such structures do not provide protection against infection or injury during disposal of the used needle. Structures of this type are shown in:
  (a) U.S. Pat. No. 3,073,307 issued to Stevens for NEEDLE HUB AND SHEATH STRUCTURE;
  (b) U.S. Pat. No. 3,333,682 issued to Burke for DISPOSABLE NEEDLE CONTAINER; and
  (c) U.S. Pat. No. 3,934,722 issued to Goldberg for STERILE NEEDLE PACKAGE.

Another needle package is shown in U.S. Pat. No. 3,021,942 issued to Hamilton for a NEEDLE PACKAGE. Hamilton recognizes the need for protection against injury and infection during disposal of a used needle and discloses a needle contained in a capped sheath prior to use which may be reinserted into the sheath and recapped after use. However, with that structure the user's hand is not adequately protected during reinsertion of the used needle and the cap may subsequently be removed to allow access to the unsanitary needle contained therein. Therefore, Hamilton does not provide adequate protection.

Other attempts to provide protection against injury and infection from direct contact with used hypodermic needles during disposal include cannister type containers. In one such cannister the used needle is inserted into an aperture and sharp blades sever the unsanitary needle in the vicinity of the needle hub. Another cannister device is disclosed in U.S. Pat. No. 4,375,849 issued to Hanifl for SYRINGE NEEDLE REMOVAL AND DISPOSAL DEVICE. The structure there disclosed includes an aperture configured to receive the unsanitary needle and facilitate rotational disengagement of the needle hub from the syringe to allow the needle to fall into the cannister. Cannister structures are generally unsatisfactory in that the cannister must either be inconveniently transported to the point of needle use or, alternatively, the exposed, unsanitary needle must be transported to the cannister. Cannister type structures often present the additional hazard that one or more needles contained therein may pierce the side wall thereof or otherwise protrude therefrom. Moreover, cannisters can often be upset while in an open position to allow used needles to spill out.

OBJECTS OF THE INVENTION

It is therefore an object of the present invention to provide a new and improved safety package for needles.

A further object of the present invention is to provide a new and improved safety needle package which may be used both to safely package a sterile needle and dispose of a used, unsanitary needle.

A still further object of the present invention is to provide a new and improved safety needle package which cannot be mislaid during use of the needle.

Another object of the present invention is to provide a new and improved needle package which does not permit access to an unsanitary needle contained therein.

These and other highly desirable and unusual results are accomplished by the present invention in an economical structure which may be disposed of with confidence that no injury or infection from the unsanitary needle will result.

Objects and advantages of the invention are set forth in part herein and in part will be obvious herefrom, or may be learned by practice with the invention, the same being realized and attained by means of the instrumentalities and combinations pointed out in the appended claims.

The invention consists of the novel parts, constructions, arrangements, combinations, steps, and improvements herein shown and described.

SUMMARY OF THE INVENTION

In accordance with the present invention, a conventional needle having a needle hub is provided with a novel needle package to safely contain the sterile needle prior to use and to securely contain the unsanitary needle after use.

The needle package in accordance with the present invention assures sterility of the needle prior to use and prevents accidental contact with and, therefore, injury and infection from the unsanitary needle after use. Advantageously, the needle package according to the present invention is connected to the needle hub and cannot be mislaid during use of the needle.

In a first preferred embodiment of the invention a base is attached to the needle hub surrounding the needle. A needle housing is hingedly attached to the base by a living hinge such that the housing may move from a first housing position removably covering the sterile needle to a second housing position exposing the needle to a third housing position securely covering the used needle such that the housing cannot thereafter readily be removed from the third position. Finger depressions are provided in the housing to facilitate movement of the housing between housing positions. Removable sealing means are provided to seal the sterile needle within the housing in the first housing position prior to use. Housing retaining means are provided to secure the housing in the third housing position so that the used needle cannot readily be accessed. The needle package is preferably molded from plastic for simple, inexpensive manufacture.

The sealing means may consist of relatively weak or otherwise frangible longitudinal and peripheral cover sections of the housing molded together with the housing. The peripheral cover portion is also integral with the base and secures the housing to the base in the first housing position. The longitudinal cover section may also extend over and be fastened to the base, particularly where a sterile seal is provided around the entire package by an external wrapper and the peripheral seal is dispensed with. Preferably a tab is provided to facilitate removal of the sealing means, thereby opening a needle aperture in the housing wall by removing the longitudinal cover and disconnecting the housing from the base other than at the hinge by removing the peripheral cover section.

The retaining means preferably consists of a hook-like protrusion extending from the inside wall of the housing. When the housing is in the first housing position the hook-like protrusion is biased against the needle such that the non-barbed side of the hook is biased against the needle. As the housing is moved to the second housing position away from the needle the biasing pressure of the needle is removed from the hook-like protrusion so that the tip of the protrusion crosses the plane of the needle. As the housing is moved from the second housing position to the third housing position the hook barb contacts the needle and the hook is pushed aside. As the barb passes the needle, the hook resiliently returns to a natural position such that the needle is hooked behind the barb. The housing cannot thereafter readily be returned to the second housing position.

In a second preferred embodiment two or more housing members are hingedly connected to the base which is, in turn, connected to the needle hub. A longitudinal cover and housing blocks integral therewith secure the housing members slightly apart. The longitudinal cover is provided with a tab to facilitate removal of the longitudinal cover and housing blocks from the needle package. The longitudinal cover provides a seal between the housing members and, together with a peripheral cover which provides a seal between the housing members and base, assures sterility of a needle enclosed in the package. Alternatively, the longitudinal cover may only secure the housing members in the spaced apart position without providing a sterile seal, in which case a sterile seal is preferably provided by an external plastic wrap enclosing the entire needle package. This obviates the need for a peripheral seal as well.

Upon removal of the longitudinal cover and housing blocks the housing members are hingedly rotated away from the needle to allow an injection to be administered. Advantageously, the housing members are provided with a housing lever consisting of housing lever arms connected to each other and to each housing member. The housing lever causes the housing members to open and close substantially in unison.

After use of the needle, the housing members are hingedly closed around the needle. Locking means are provided for securely locking the housing members so that the used, unsanitary needle is fully enclosed. The locking means may consist of locking pins provided on one housing member to engage corresponding locking pin holes in another housing member. Preferably, the locking pins and/or the locking pin holes are ribbed to substantially prevent subsequent disengagement of the locking pins from the locking pin holes.

In use, the needle package according to either preferred embodiment is opened to access the sterile needle by removing the sealing means, including the external wrapper and/or longitudinal cover. The housing or housing members are hingedly moved aside to permit use of the sterile needle. After the needle has been used the housing or housing members are hingedly returned to cover the used needle and the locking means are engaged to prevent the used needle from readily being reaccessed. The needle thus contained may then be disposed of safely. Moreover, once the sealing means has been compromised all persons are alerted that the needle therein has already been accessed and is not fit for use.

Of course, it is also contemplated that sterile seals could be provided by both an external wrapper and the longitudinal and peripheral cover sections. In this manner the sterile needle package could be removed from the wrapper and attached to a syringe while the sterility of the needle itself is further protected by the needle package until just prior to use.

It will be apparently from the foregoing general description that the objects of the invention specifically enumerated herein are accomplished by the invention as here embodied.

Thus, as one advantage of the present invention a needle package is provided which safely contains a sterile needle prior to use and which also contains the used, unsterile needle after us to prevent accidental injury and infection.

As a further advantage of the present invention the used needle advantageously cannot readily be reaccessed after the needle housing has been closed.

As yet a further advantage of the present invention hospital personnel are alerted to whether the needle therein has previously been accessed and is, therefore, not fit for use.

As yet a further advantage of the present invention a needle is both protected while sterile and securely contained after use in a needle package which remarkably does not become disassociated from the needle and needle hub structure during use. Thus, the protection provided by the needle package according to the present invention cannot be inadvertently frustrated by misplacing the needle package during use of the needle.

It will be understood that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate preferred embodiments of the product of the present invention, and together with the description serve to explain the principles of the invention, in which.

DETAILED DESCRIPTION OF THE PREFERRED EMBODIMENTS

Figure 1:
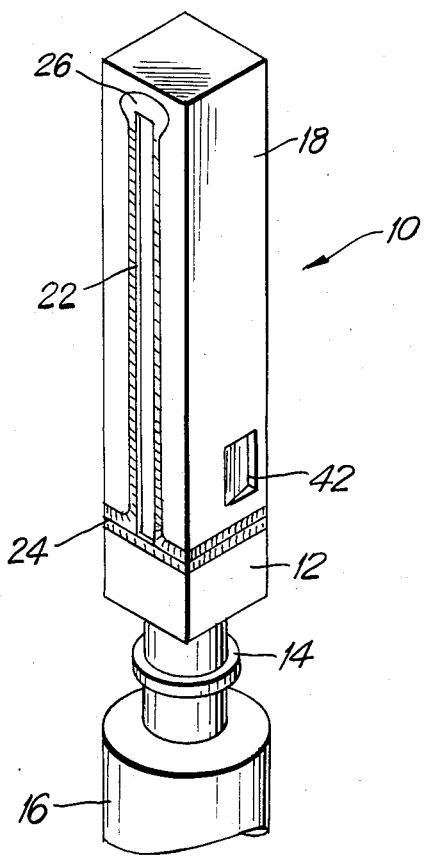
FIG. 1 is a perspective view of a needle package in accordance with a first preferred embodiment of the present invention, shown attached to a syringe.
Figure 2:
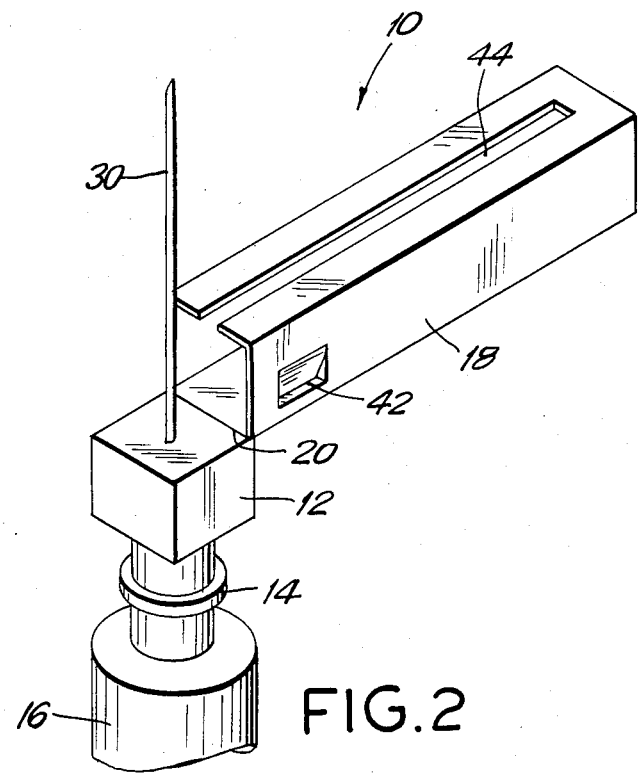
FIG. 2 is a perspective view of the needle package illustrated in FIG. 1, shown in the open position to permit access to a needle.
Figure 3:
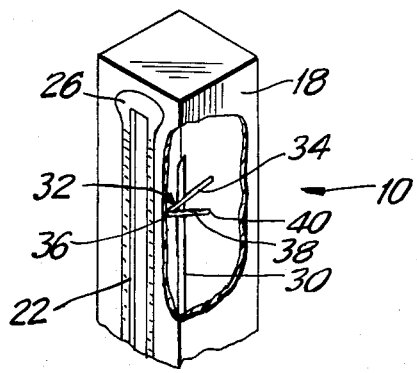
FIG. 3 is a partial cut away view of the needle package illustrated in FIG. 1, showing the needle locking hook biased in the unlocked position.

Referring now more particularly to FIGS. 1-4 of the accompanying drawings, there is shown a needle package in accordance with a first preferred embodiment of the present invention, indicated generally by reference numeral 10. Needle package 10 has a base 12 attached to a needle hub 14, here shown attached to a syringe 16. A needle housing 18 is connected to base 12 by a living hinge 20. Housing 18 is provided with removable sealing means to provided a seal around a sterile needle contained therein. The sealing means may consist of a longitudinal cover 22 and a peripheral cover 24. Moreover, a sterile seal may be provided over needle package 10, as a whole, by enclosing the needle package within a sealed plastic pouch. Where a sealed pouch is provided peripheral seal 24 may be dispensed, in which case longitudinal cover 22 preferably extends onto base 12. Cover 22 is provided with a gripping tab 26 to facilitate removal of the longitudinal cover from the housing, thereby exposing a needle access port 44. Removal of longitudinal and peripheral cover sections 22, 24 permits housing 18 to rotate relative to base 12 about hinge 20. As shown in FIG. 3, needle 30 becomes exposed for use through needle access port 44 by rotating housing 18 about hinge 20. After the needle has been used housing 18 is again rotated about hinge 20 to return the housing to a position enclosing the needle. Locking means consisting of a hook-like protrusion attached to the inner wall of housing 18 engages needle 30 to prevent subseguent rotation of housing 18 about hinge 20, thereby substantially preventing needle 30 from being reaccessed.

Figure 4:
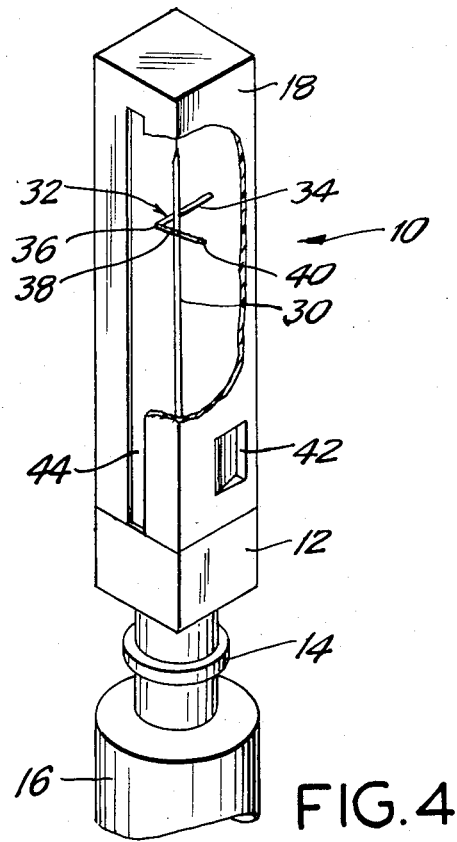
FIG. 4 is a partial cut away view of a needle package in accordance with the first preferred embodiment of the present invention, showing the needle package in the locked position.

As shown more particularly in FIGS. 3-4, the hook-like locking protrusion 32 extending from the inner wall of housing 18 is biased against sterile needle 30 with the non barbed side of hook stem 34 contacting needle 30. Hook 32 becomes disassociated from needle 30 as housing 18 is rotated to gain access to the sterile needle. After the biasing force of the needle upon the locking protrusion has thus been removed the hook-like protrusion assumes a natural position, causing the tip 36 of hook stem 34 to cross the plane of needle 30. Hook tip 36 cannot prematurely cross the needle plane prior to opening the needle package since, prior to opening, housing 18 is anchored relative to base 12 by frangible peripheral cover seal 24 and/or the extension of longitudinal cover 22 onto base 12. After the needle has been used housing 18 is rotated about hinge 20 to cover needle 30. Needle 30 contacts barb 38 of hook-like protrusion 32 and, as housing 18 is urged completely over needle 30, resilient barb 38 and hook stem 34 are flexed to allow needle 30 to pass thereover. As tip 40 of barb 38 passes needle 30 both barb 38 and stem 34 resiliently return to a natural position in which the needle is trapped behind barb 38. Thereafter, housing 18 cannot readily be rotated to again expose needle 30.

Referring more particularly to FIG. 1, base 12 is connected to needle hub 14. As here shown, needle hub 14 may be provided pre-attached to syringe 16 or, alternatively, may be attached to syringe 16 just prior to use. Housing 18 extends longitudinally from base 12 to enclose the needle attached to and extending from needle hub 16. Housing 18 is connected to base 12 by a living hinge 20 (see FIG. 2) and by frangible peripheral seal 24. A longitudinal sealing cover 22 is provided extending along the side wall of housing 18 over a needle access port opposite hinge 20 and substantially corresponding to the projected plane of the needle contained within the housing. A gripping tab 26 is provided on longitudinal sealing cover 22 and finger slots or depressions 42 are provided on housing 18 to facilitate opening the needle package.

FIG. 2 shows the needle package illustrated in FIG. 1 in the open position after the longitudinal sealing cover and peripheral seal have been removed and compromised, respectively. Needle access port 44 created by removal of the longitudinal sealing cover allows housing 18 to be rotated to expose needle 30. Here, housing 18 is shown rotated about hinge 20 through approximately 90° of rotation relative to base 12 such that needle 30 has emerged through needle port 44 and is exposed ready for use.

FIG. 3, a partial cut away perspective view of the needle package shown in FIG. 1, shows the preferred hook-type locking means biased in the unlocked position. Locking hook 32 protrudes radially inward from the housing wall toward needle 30. In the unlocked position shown the resilient locking hook is biased so that needle 30 contacts the side of hook stem 34 opposite hook barb 38.

FIG. 4 is a partial cut-away perspective view of the needle package in which housing 18 has been rotated from the open position shown in FIG. 2 to the upright position shown covering the needle. The preferred hook-type locking means is shown in the locked position with needle 30 trapped behind hook barb 38. Thus, subsequent rotation of housing 18 about the hinge is substantially prevented so that needle 30 cannot thereafter become exposed or be reaccessed.

In use, needle hub 14 is connected to syringe 16 in a known fashion such as a Luer lock. Tab 26 is pulled to remove longitudinal cover 22 and expose needle port 44. Peripheral seal 24 is either removed together with longitudinal cover 22 in a single motion or is compromised as housing 18 is rotated about hinge 20. As housing 18 is rotated about hinge 20 needle 30 becomes disassociated from biasing contact with hook stem 34 (See FIG. 3) and hook stem tip 36 crosses the plane of needle 30. As housing 18 is further rotated about hinge 20 housing 18 leaves the first, unlocked position covering needle 30 and needle port 44 passes over stationary needle 30 to expose the needle in a suitable position ready for use. Housing 18 remains conveniently attached to base 12 by hinge 20 without interfering with use of needle 30. Finger depressions or slots 42 are provided on housing 18 to facilitate rotation of housing 18 about hinge 20.

After the needle has been used to administer an injection, housing 18 is rotated about hinge 20 toward the upright position covering needle 30. During this rotation of the housing needle access port 44 again passes over needle 30. As housing 18 is further rotated needle 30 again contacts the hook-like locking means. However, since the biasing force of the needle against the hook stem is no longer present and hook stem tip 36 has previously crossed the needle plane, needle 30 contacts hook barb 38 as housing 18 is rotated to the upright position covering the used needle. Barb 38 and stem 34 are sufficiently flexible to be pushed aside by needle 30 as the housing is closed. As needle 30 passes tip 40 of barb 38 the barb and stem resiliently resume a natural position whereby needle 30 is held behind barb 38 of hook 32. Thus, the needle package is effectively locked so that the housing cannot thereafter readily be rotated to reaccess the used, unsanitary needle. The needle package containing the unsanitary needle can then be disposed of either together with or separately from the syringe. The needle package may be disposed of either directly in a trash receptacle or in a further safety disposal unit, such as a cannister type receptacle.

Thus, the sterile needle is protected prior to use and administering personnel are protected from injury and infection from needle contact both before and after needle use. Exposure of the needle is desirably limited to the period of use. These remarkable advantages are obtained by the novel needle package without the possibility that the disposal unit will become misplaced during use of the needle, thereby frustrating the object of protecting against the hazards of post injection exposed needles.

A second preferred embodiment in accordance with the present invention is shown in FIGS. 5-11 with reference numerals corresponding to FIGS. 1-4. In this embodiment needle package 10 having base 12 attached to needle hub 14 is provided with two needle housing members 50, 52 hingedly attached to base 12.

Figure 5:
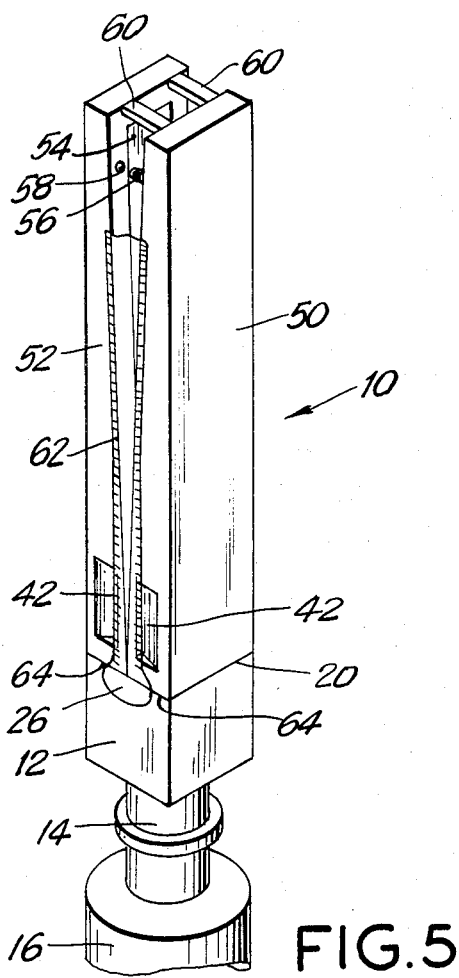
FIG. 5 is a partial cut away perspective view of a needle package in accordance with a second preferred embodiment of the present invention, shown attached to a syringe.

Referring more particularly to FIG. 5, a cut away perspective view of a needle package in accordance with the second preferred embodiment of the present invention, needle package 10 is provided with housing members 50, 52 having needle grooves or openings 54. Housing members 50, 52 are secured to base 12 by hinges 20 and base 12 is attached to needle hub 14. Needle hub 14 is removably fastened to syringe 16 in a known fashion such as by a Luer lock. Housing members 50, 52 are provided with locking means, preferably one or more locking pins 56 and locking pin holes 58 provided on each housing member. One or more housing blocks 60 and longitudinal sealing cover 62 are provided to secure housing members 50, 52 sufficiently apart prior to use such that locking pins 56 do not prematurely engage locking pin holes 58. Housing blocks 60 need not be securely attached to housing members 50, 52 as long as the housing blocks are positioned between the housing members to assure adequate spacing of the housing members. Gripping tab 26 is provided to facilitate removal of longitudinal cover 62. Preferably, housing blocks 60 are attached to cover 62 so that, as cover 62 is removed by pulling tab 26 cover 62 draws housing blocks 60 away from housing members 50, 52.

Figure 6:
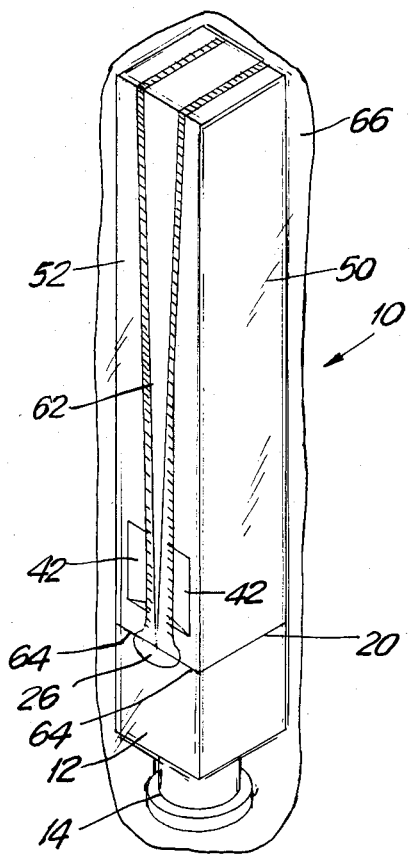
FIG. 6 is a perspective view of a needle package in accordance with a second preferred embodiment of the invention, shown sealed within a transparent sterile wrapper.

Preferably, longitudinal cover 62 provides a sterile seal between housing members 50, 52 and a frangible sterile seal is provided at the space or juncture 64 between housing members 50, 52 and base 12 other than at hinges 20. Alternatively, as shown in FIG. 6, needle package 10 as a whole may be wrapped in a sterile wrap 66, such as a sealed plastic pouch. In this case, longitudinal cover 62 need not provide a sterile seal between housing members 50, 52 and no sterile seal is required at juncture 64. Of course, the sterile seal of cover 62 and at juncture 64 could also be provided so that sterility of the needle could be preserved prior to use but after the needle has been removed from the pouch and attached to a syringe. A syringe could also be sealed within pouch 66 so that both the needle package and syringe are conveniently available to the user in a single sterile pouch.

Figure 7:
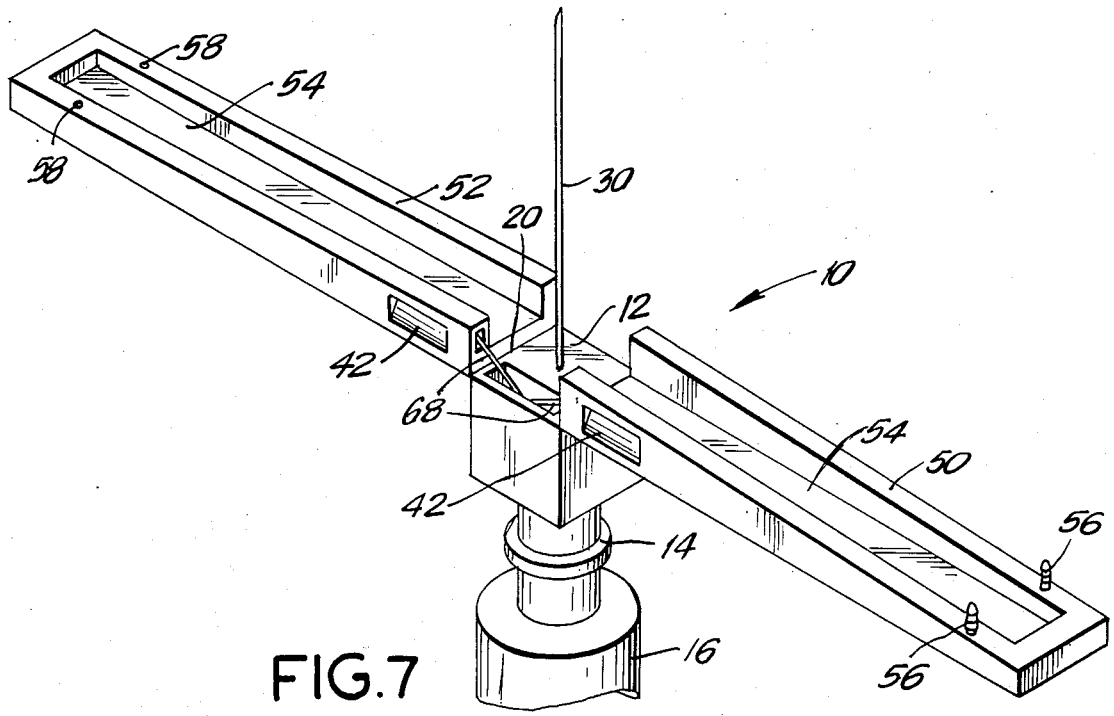
FIG. 7 is a perspective view of the needle package illustrated in FIGS. 5-6, shown in the open position.

FIG. 7 illustrates the needle package 10 shown in FIGS. 5-6 in the open position ready for use. The external sterile pouch, if any, longitudinal cover, and housing blocks have been removed and housing members 50, 52 have been rotated about hinges 20 into the open position shown. Needle 30 is exposed ready for use. Preferably, a housing lever is provided to assure that housing members 50, 52 rotate about hinges 20 substantially in unison.

Figure 8:
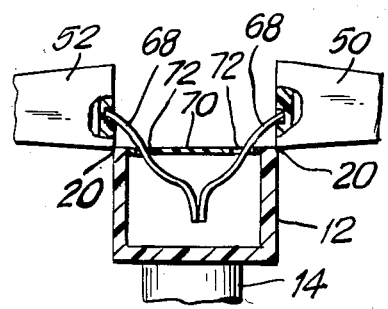
FIG. 8 is a partial cross section view of the needle package illustrated in FIG. 7, showing a housing lever.
Figure 9:
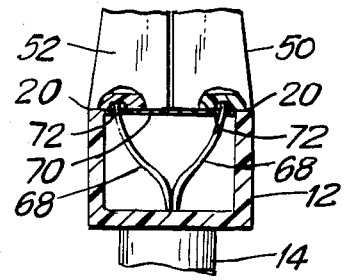
FIG. 9 is a partial cross section view of the needle package illustrated in FIG. 8, shown in the closed position.

As shown in FIG. 8, housing lever arms 68 consist of flexible plastic fibers attached to each housing member and to each other within a hollow space of base 12. A strut or cross bar 70 may be provided across the base opening 72 through which housing levers arms 68 protrude. Strut 70 acts to limit the degree of rotation of housing members 50, 52 about hinges 20 by limiting the extent of travel of housing lever arms 68. As shown in FIG. 9, housing lever arms 68 recede into base 12 when housing members 50, 52 are in an upright, closed position.

Figure 10:
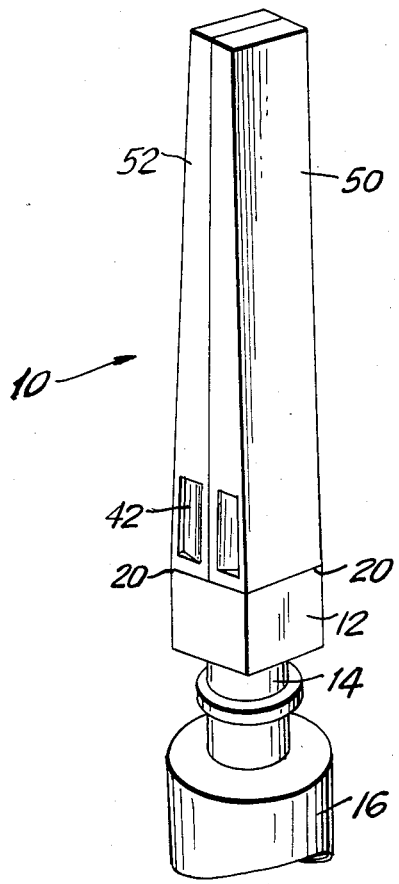
FIG. 10 is a perspective view of the needle package illustrated in FIGS. 5-6, shown in the closed, locked position.

FIG. 10 is a perspective view of the needle package of FIGS. 5-9 shown in the closed, locked position. Housing members 50, 52 are shown drawn together to fully enclose the needle attached to needle hub 14. The locking means (not visible) are engaged to secure housing members 50, 52 and, hence, needle package 10 in the closed position so that the needle package containing the unsanitary needle may be safely transported and disposed of.

Figure 11:
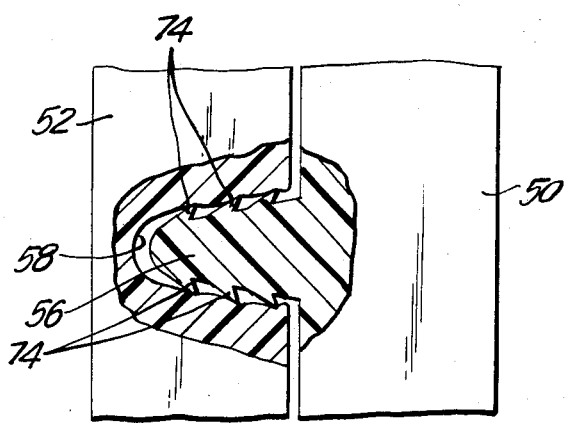
FIG. 11 is a partial cross-section view of the needle package illustrated in FIG. 10, showing a locking pin engaging a locking pin hole.

FIG. 11 is a cross section view of locking pin 56 in the locked position within locking pin hole 58. Preferably, locking pin 56 is provided with one or more radially projecting ribs 74 to distort and firmly engage the walls of locking pin hole 58, thereby making reopening of the locked package very difficult and unlikely. Of course, hook-type locking means as discussed above in relation to the first preferred embodiment could be provided within needle grooves 54 to lock the housing members of the second preferred embodiment in the closed, locked position.

Advantageously the base, hinge, longitudinal cover, gripping tab, locking means and peripheral seal, if any, may all be molded together of plastic, such as polyethylene, for ease of manufacture. Preferably, the base is molded together with the needle hub and may simply comprise an extension thereof. The longitudinal cover and peripheral seal may simply comprise relatively weak sections of the molded needle package.

In use, the sterile wrapper, if any, is removed and the longitudinal cover 22 and housing blocks 60 are removed by pulling gripping tab 26. The peripheral seal at juncture 64, if any, is compromised and housing members 50,52 are rotated about hinges 20 away from needle 30. Housing members 50, 52 are forced together to engage the locking pins 56 in locking pins 58. The preferred radial ribs 74 prevent the needle package 10 from readily being reopened. Thus, the needle may be disposed of with confidence that the needle will not cause accidental injury or infection and will not inadvertently be reaccessed. Reaccessing the used needle within the closed, locked needle package is also sufficiently difficult to discourage drug abusers from trying to access and use the unsanitary needle.

To the extent not already indicated, it also will be understood by those of ordinary skill in the art that any of the various specific embodiments herein described and illustrated may be further modified to incorporate features shown in any of the other specific embodiments, as decribed.

The invention in its broader aspects therefor is not limited to the specific embodiments herein shown and described but departures may be made therefrom within the scope of the accompanying claims, without departing from the principles of the invention and without sacrificing its chief advantages.

I claim:

1. A safety needle package comprising:
   a base secured to a needle hub, said needle hub having a needle attached thereto;
   a housing hingedly attached to said needle hub, said housing assuming a first housing position longitudinally enclosing said needle prior to use of said needle, a second housing position hingedly rotated away from said needle and exposing said needle for use, and a third housing position longitudinally enclosing said needle after use of said needle;
   removable securing means for removably securing said housing in said first housing position by preventing rotation of said housing about said hinge prior to removal of said removable securing means, said housing being freely rotatable about said hinge and movable from said first housing position to said second housing position after said removable securing means is removed; and
   housing locking means for securing said housing in said third housing position enclosing said needle after use of said needle so that said housing cannot be moved from said third housing position to said second housing position, thereby preventing said needle from thereafter being re-exposed and re-accessed.

2. The safety needle package according to claim 1 wherein said housing is hingedly attached to said needle hub by a living hinge.

3. The safety needle package according to claim 2 wherein said housing is provided with a longitudinal needle access aperture in the longitudinal side of said housing opposite the longitudinal side of said housing connected to said hinge.

4. The safety needle package according to claim 3 wherein said securing means further comprises a longitudinal cover section disposed over said longitudinal needle access aperture.

5. The safety needle package according to claim 4 wherein said longitudinal cover extends over and is attached to said base.

6. The safety needle package according to claim 4 wherein said longitudinal cover section is provided with a gripping tab.

7. The safety needle package according to claim 4 wherein said securing means further comprises a peripheral cover section between said housing and said base other than at said hinge.

8. The safety needle package according to claim 7 wherein said longitudinal and peripheral cover sections provide a sterile seal between said housing and said base.

9. The safety needle package according to claim 1 wherein said housing locking means further comprises a hook-like resilient projection attached to an inner wall of said housing.

10. A safety needle package comprising:
    a base secured to a needle hub, said needle hub having a needle attached thereto;
    a housing hingedly attached to said needle hub, said housing assuming a first housing position longitudinally enclosing said needle prior to use of said needle, a second housing position hingedly rotated away from said needle and exposing said needle for use, and a third housing position longitudinally enclosing said needle after use of said needle;
    removable securing means for removably securing said housing in said first housing position by preventing rotation of said housing about said hinge prior to removal of said removable securing means, said housing being freely rotatable about said hinge and movable from said first housing position to said second housing position after said removable securing means is removed; and
    housing locking means consisting of a hook-like resilient projection attached to an inner wall of said housing, said hook-like projection assuming an unlocked position biased against said needle corresponding to said first housing position, an unlocked, unbiased position corresponding to said second housing position, and a locked position corresponding to said third housing position to secure said housing in said third housing position so that said housing cannot be moved from said third housing position to said second housing position, thereby preventing said needle from thereafter being re-exposed and re-accessed.

11. The safety needle package according to claim 10 wherein said hook-like projection includes a barb, said barb being disposed across said needle in said locked position.

12. A safety needle package comprising:
a base secured to a needle hub, said needle hub having a needle attached thereto;
a housing hingedly attached to said needle hub, said housing assuming a first housing position longitudinally enclosing said needle prior to use of said needle, a second housing position hingedly rotated away from said needle and exposing said needle for use, and a third housing position longitudinally enclosing said needle after use of said needle;
removable securing means for removably securing said housing in said first housing position by preventing rotation of said housing about said hinge prior to removal of said removable securing means, said housing being rotatable about said hinge and movable from said first housing position to said second housing position after said removable securing means is removed; and
housing locking means consisting of a hook-like resilient projection attached to an inner wall of said housing for securing said housing in said third housing position enclosing said needle after use such that said housing locking means prevents said housing from being moved from said third housing position to said second housing position, thereby preventing said needle from thereafter being re-exposed and re-accessed, said hook-like projection lockingly engaging said needle when said housing is in said third housing position.

13. The safety needle package according to claim 10 wherein said housing is hingedly attached to said needle hub by a living hinge.

14. The safety needle package according to claim 13 wherein said housing is provided with a longitudinal needle access aperture in the longitudinal side of said housing opposite the longitudinal side of said housing connected to said hinge.

15. The safety needle package according to claim 14 wherein said securing means further comprise a longitudinal cover section attached to said housing and disposed over said needle access aperture.

16. The safety needle package according to claim 15 wherein said longitudinal cover extends over and is attached to said base.

17. The safety needle package according to claim 15 wherein said longitudinal cover section is provided with a gripping tab.

18. The safety needle package according to claim 15 wherein said securing means further comprise a peripheral cover section between said housing and said base other than at said hinge.

19. The safety needle package according to claim 18 wherein said longitudinal and peripheral cover sections provide a sterile seal between said housing and said base.

20. The safety needle package according to claim 12 wherein said housing is hingedly attached to said needle hub by a living hinge.

21. The safety needle package according to claim 20 wherein said housing is provided with a longitudinal needle access aperture in the longitudinal side of said housing opposite the longitudinal side of said housing connected to said hinge.

22. The safety needle package according to claim 21 wherein said securing means further comprise a longitudinal cover section attached to said housing and disposed over said needle access aperture.

23. The safety needle package according to claim 22 wherein said longitudinal cover extends over and is attached to said base.

24. The safety needle package according to claim 22 wherein said longitudinal cover section is provided with a gripping tab.

25. The safety needle package according to claim 22 wherein said securing means further comprise a peripheral cover section between said housing and said base other than at said hinge.

26. The safety needle package according to claim 25 wherein said longitudinal and peripheral cover sections provide a sterile seal between said housing and said base.

27. A method for preventing accidental contact with a needle comprising the steps of;
(i) providing a safety needle package including:
a base secured to a needle hub, said needle hub having a needle attached thereto;
a housing hingedly attached to said needle hub, said housing assuming a first housing postion longitudinally enclosing said needle prior to use of said needle, a second housing position hingedly rotated away from said needle and exposing said needle for use, and third housing position longitudinally enclosing said needle after use of said needle;
removable securing means for removably securing said housing in said first housing position by preventing rotation of said housing about said hinge prior to removal of said removable securing means, said housing being freely rotatable about said hinge and movable from said first housing position to said second housing position after said removable securing means is removed; and
housing locking means for securing said housing in said third housing position enclosing said needle after use of said needle so that said housing cannot be moved from said third housing position to said second housing position, thereby preventing said needle from thereafter being re-exposed and re-accessed;
(ii) removing said removable securing means;
(iii) rotating said hinged housing from said first housing position to said second housing position to expose said needle for use;
(iv) rotating said housing from said second housing position to said third housing position after said needle has been used;
(v) engaging said housing locking means to securely lock said housing in said third housing so that said housing cannot thereafter be moved from said third housing position to said second housing position thereby preventing said safety needle package from being reopened.

* * * * *

UNITED STATES PATENT AND TRADEMARK OFFICE
CERTIFICATE OF CORRECTION

PATENT NO. : 4,664,259

DATED : May 12, 1987

INVENTOR(S) : Robert Landis

It is certified that error appears in the above-identified patent and that said Letters Patent is hereby corrected as shown below:

Column 4, line 50, "us" should read --use--

Column 10, line 15, after "section" insert --attached to said housing--

Signed and Sealed this

Fifteenth Day of September, 1987

Attest:

DONALD J. QUIGG

*Attesting Officer*  *Commissioner of Patents and Trademarks*